United States Patent
Cuming

(10) Patent No.: US 6,559,659 B2
(45) Date of Patent: May 6, 2003

(54) MATRIC SOIL MOISTURE SENSING DEVICE

(76) Inventor: Kenneth James Cuming, 68 Robinson Road, Hawthorn. Victoria 3122. (AU)

(*) Notice: Subject to any disclaimer, the term of this patent is extended or adjusted under 35 U.S.C. 154(b) by 0 days.

(21) Appl. No.: 09/939,939

(22) Filed: Aug. 27, 2001

(65) Prior Publication Data

US 2002/0167412 A1 Nov. 14, 2002

(30) Foreign Application Priority Data

May 14, 2001 (AU) ............................................. PR4963

(51) Int. Cl.⁷ ............................................. G01R 27/26
(52) U.S. Cl. ............................................. 324/694; 73/73
(58) Field of Search ............................ 324/694, 696, 324/609, 664; 137/78.3; 73/73

(56) References Cited

U.S. PATENT DOCUMENTS

| | | | |
|---|---|---|---|
| 4,137,931 A | 2/1979 | Hasenbeck | 137/78.3 |
| 4,216,789 A | 8/1980 | Hasenbeck | 137/78.3 |
| 4,513,608 A | 4/1985 | Cuming | 73/73 |
| 4,531,087 A | 7/1985 | Larson | 324/696 |
| 4,561,293 A | 12/1985 | Richards | 73/73 |
| 4,693,419 A | 9/1987 | Weintraub et al. | 239/63 |
| 4,718,446 A | 1/1988 | Simpson | 137/78.3 |
| 4,785,843 A | 11/1988 | Nicholson | 137/78.3 |
| 4,796,654 A | 1/1989 | Simpson | 137/78.3 |
| 4,852,802 A | 8/1989 | Iggulden et al. | 239/64 |
| 4,879,498 A | 11/1989 | Shinohara et al. | 318/254 |
| 4,892,113 A | 1/1990 | Fattahi | 137/78.3 |
| 4,952,868 A | 8/1990 | Scherer, III | 324/664 |

*Primary Examiner*—Christine Oda
*Assistant Examiner*—Vincent Q. Nguyen
(74) *Attorney, Agent, or Firm*—Alston & Bird LLP

(57) ABSTRACT

A soil moisture sensing device for sensing moisture levels in a particular soil area. The device has a porous body with at least two zones, a first one of the zones having pore sizes that approximate a range of pores in typical soils, a second one of the zones having pores arranged to be small enough to remain hydrated at higher matric tensions. The first and second zones contain respective electrodes, each being paired with an electrode common to both zones. As the matric tension of the soil solution increases, the pores within the first zone dehydrate causing increased resistance between the first electrode and the common electrode while the pores in the second zone remain hydrated, the resistance between the second electrode and the common electrode changing only in response to conductivity of the soil solution in the second zone.

15 Claims, 2 Drawing Sheets

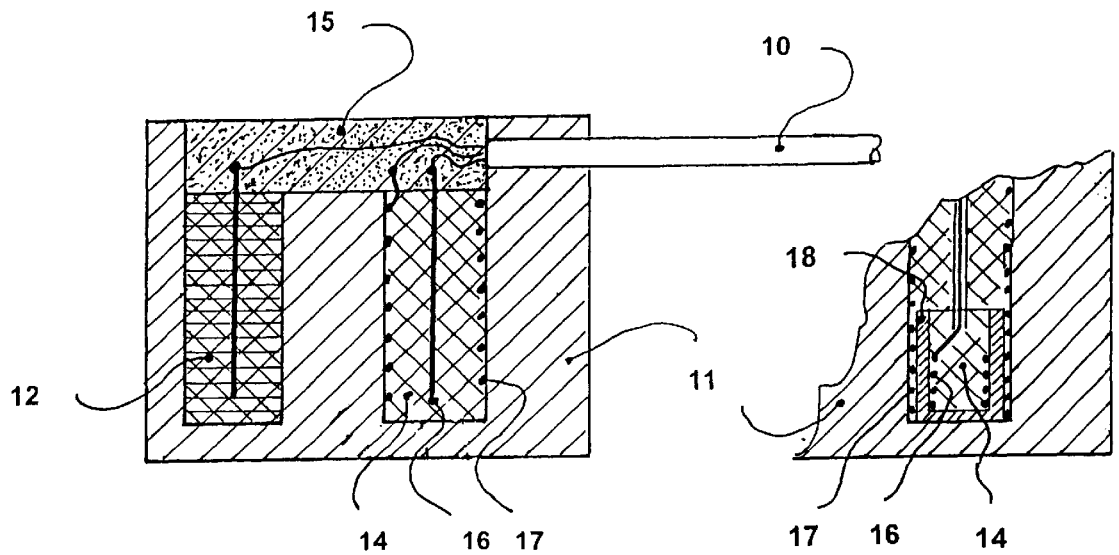
FIGURE 1a
FIGURE 1b
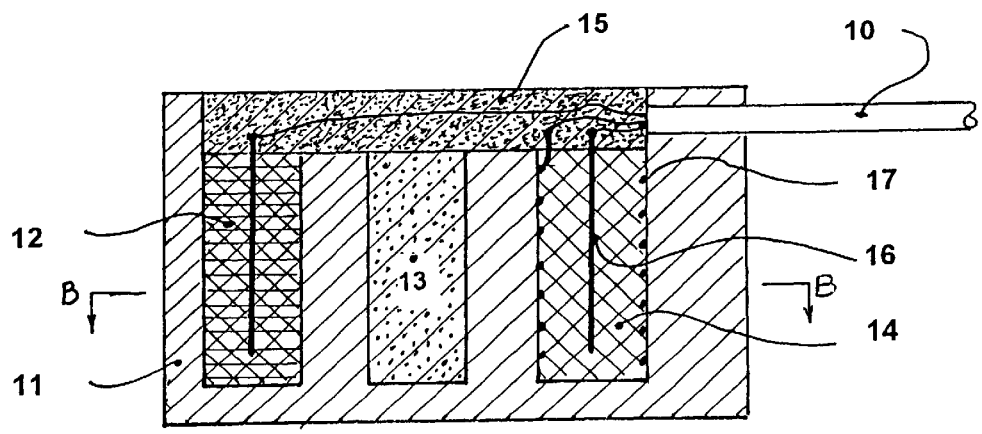
FIGURE 2a
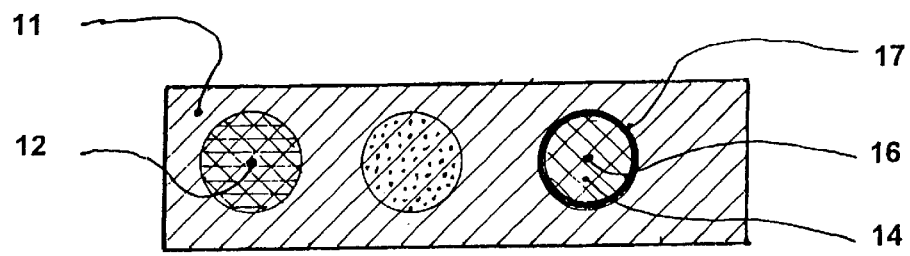
FIGURE 2b

MATRIC SOIL MOISTURE SENSING DEVICE

BACKGROUND OF THE INVENTION

1. Field of the Invention

The present invention relates to devices for sensing moisture content in soils and to thereby monitor it and/or control the supply of water to desired areas in agricultural and horticultural situations and is the culmination of a wide experience with a commercially practical sensor.

2. Description of Related Art

U.S. Pat. No. 4,513,608 discloses one form of sensing device, hereafter referred to as Type "A", having two separate porous zones one with relatively large pores which approximate the range of field soil pores, the second with fine pores. A pair of electrodes in each zone thereby forms a current path through the respective porous zones. In use the device is placed in an in ground position such that ground moisture is in intimate contact with it to maintain a reliable hydraulic and chemical equilibrium with the porous zones. The electrical resistance in the current paths through the respective porous zones is then used to indicate in ground soil moisture levels. This device has proven to remain accurate and reliable in practice and a large number have been applied in commercial use however it requires costly ceramic materials, is labour intensive and is difficult and expensive to manufacture.

There have been many other moisture content sensor designs proposed using various techniques including electrical resistance, capacitance, reflectrometry and thermal diffusivity, all of which have introduced their own problems when operating in such a physically, chemically and biologically hostile environment as prevails in field soils.

As examples of electrical resistance, U.S. Pat. Nos. 4,892,113, 4,879,498, 4,852,802, 4,796,654, 4,785,843, 4,718,446 and 4,693,419 all relate to bare electrodes directly in contact with the soil which sense an increase in electrical resistance as the soil dries and a decrease as it becomes moist. This principle, referred to as Type "B", is useful as long as other factors remain stable however the wide swings in the electrical conductivity (EC) of the soil solution which drops with plant uptake, rainfall, irrigation or increase in soil temperature and rises with fertilisation, water borne salts or decrease in soil temperature, can produce resistance changes many times greater than the wet to dry changes masking them to an unacceptable degree also it experiences difficulty in maintaining a reliable area of contact with representative soil, make it quite impractical as an accurate moisture monitor.

U.S. Pat. Nos. 4,952,868, 4,216,789 and 4,531,087 introduce a moisture permeable retainer for a controlled media in which the moisture resistance is determined. Referred to as Type "C", the retainer presents problems of hydrophobic barrier to moisture movement into the media. These types also do not include solution conductivity compensation to solve the problems of Type "B" even though a subsequent refinement to U.S. Pat. No. 4,531,087 introduces a pellet of a low solubility salt to ionise and mask the soil solution conductivity effect. This modification, referred to as Type "D", is only partially successful and the pellet progressively dissolves.

U.S. Pat. No. 4,137,931 utilising a Type "C" sensor introduces a second Type "C" sensor in the irrigation water supply and again in combination alongside the first sensor aimed at control of leaching and not proposed or modified or connected as a means of compensating the first sensor for change in EC of the soil solution. This sensor combination is referred to as Type "E".

U.S. Pat. No. 4,561,293 combines a Type "C" retainer like design with a fine media resistance element to compensate for changes in EC of the soil water solution. This design referred to as Type "F" has basic similarities to Type "A" but practical design problems associated with maintaining moisture movement through the retainer, blockage of its necessarily small pores, the small area of its soil moisture contact and no electrical isolation from the soil potentials prevented reliable operation except under laboratory conditions.

The foregoing description of prior art devices should not be taken as indicating any of the devices are necessarily part of the general knowledge in this industry.

The objective of the present invention is to provide a new moisture sensing device, and preferably associated equipment, that will enable the device to operate accurately enough to control irrigation efficiently over a wide range of soil types and soil solution electrical conductivities that will avoid costs associated with sensors of the type described in U.S. Pat. No. 4,513,608.

BRIEF SUMMARY OF THE INVENTION

In accordance with the present invention, there is provided a soil solution sensing device including a body formed from porous material which, in use, is placed in intimate hydraulic conduction with soil in an area under surveillance, said body forming a first zone having pore sizes that approximate a range of pores in typical soils, a second zone being formed within said first zone having pores arranged to be small enough to remain hydrated at matric tensions of the soil solution significantly above those which cause the first zone to dehydrate, said first zone containing a first electrode and said second zone containing a second electrode, each of which are paired with an electrode common to both said zones whereby, as the matric tension of the soil solution in the soil in the surveillance area increases, the pores within the first zone progressively dehydrate causing electrical resistance between the first electrode and the common electrode to progressively increase while the pores in the second zone remain hydrated such that the electrical resistance between the second electrode and the common electrode changes only in response to conductivity of the soil solution in the pores of the second zone.

In pursuing the wide commercial practical success of the Type "A" sensor design and in addressing its cost problem, the new sensor has been designed to achieve an improved performance at a fraction of its cost. Such features of the Type "A" sensor as its ability to operate over the wide range of soil solution electrical conductivities (EC) and in a preferred aspect, its technique for electrical isolation from the soil have been improved and retained.

The new design conveniently provides a single electrode in each zone, each of which pair with a single common electrode which may be designed as an electrically isolating shield between the respective zones. This reduces the size of the ceramic block and preferably introducing a void between the first zone electrode and the common electrode, the matric tension to electrical resistance response can be biassed. Lower cost body materials may also be used. The design of the common and preferably shielding electrode eliminates one electrode, simplifies assembly and enables a reduction in sensor field cables from 4 cores to 3 cores.

In preferred aspects, this technique has been further refined by developing a concept for a soil type selector to optimise setting up of the device according to soil type. This present design eliminates most of the high cost components of Type "A" and the hydraulic barriers of Type "C" whilst retaining the EC compensation and the magnetic isolation of Type "A" and by introducing a convenient means of soil type selection.

BRIEF DESCRIPTION OF THE SEVERAL VIEWS OF THE DRAWINGS

Several embodiments of the present invention are hereafter described with reference to the accompanying drawings, in which:

FIG. 1a is a longitudinal cross-sectional view of a first preferred embodiment of a sensing element according to this invention;

FIG. 1b is a partial longitudinal cross-sectional view showing a second preferred embodiment which is otherwise similar to FIG. 1a;

FIG. 2a is a longitudinal cross-sectional view of a third preferred embodiment of a sensing element according to this invention;

FIG. 2b is a transverse cross-sectional view of the sensing element shown in FIG. 2a taken along line B—B.

DETAILED DESCRIPTION OF THE INVENTION

Figure 3:
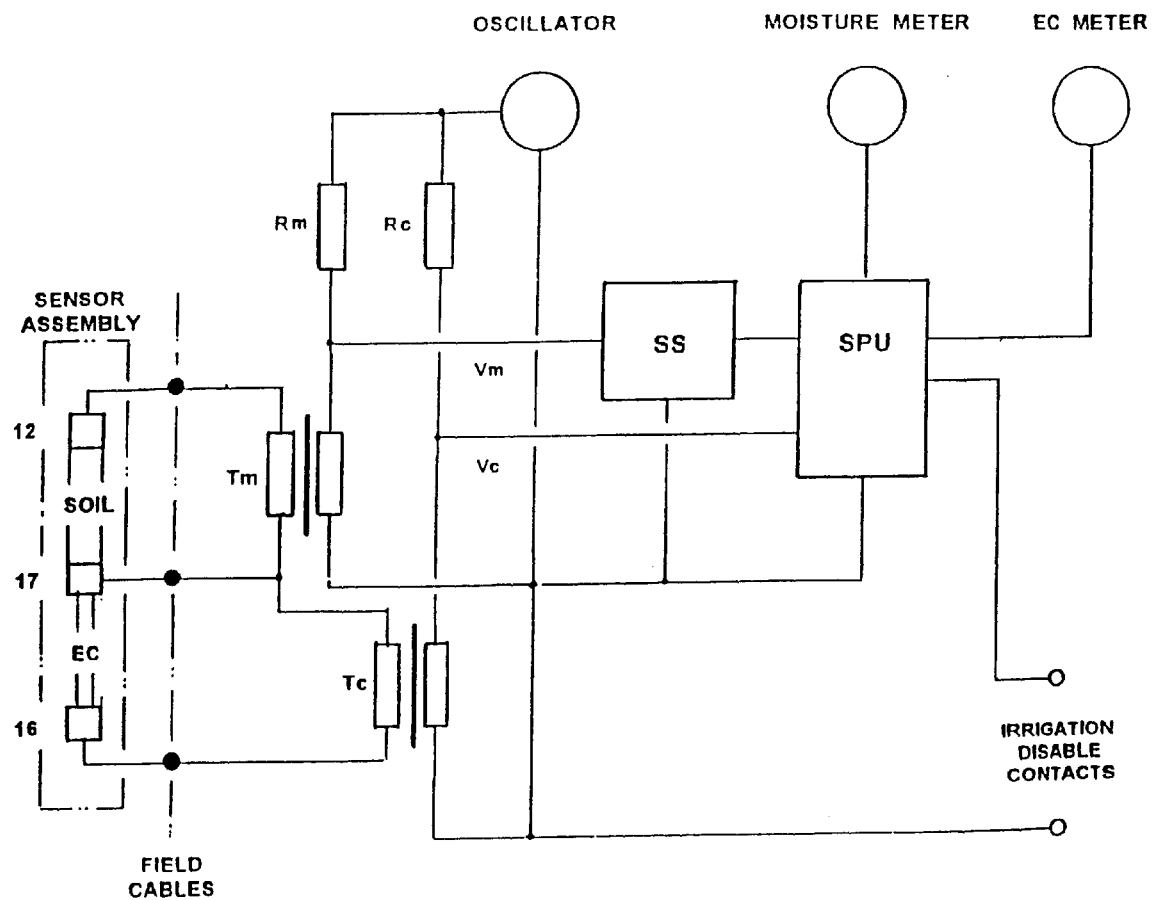
FIG. 3 is a circuit diagram utilising a sensing element according to this invention.

In the preferred embodiment illustrated in FIG. 1a, the sensing element includes a block of porous, stable, electrically insulating media 11 (hereinafter referred o as "block" or "body") with a pore size distribution ranging from 5 to 40 microns corresponding to a capillary tension range approximating 40 down to 10 Kpa depending on particle shape. The pore sizes of the block 11 generally approximate a range of pore sizes in typical soils. The majority of its external surfaces are, in use, being in intimate hydraulic conduction with the soil under surveillance to provide a reliable moisture transfer from the soil into the block 11. This block has two internal cavities with one being used to form a first electrode 12, the other being filled with fine insulating media 14, which preferably has pores smaller than 2 microns and contains a second electrode 16. A common electrode 17, which may be in the form of a helical coil or a cylindrical mesh is located between the media 14 and the surrounding porous material of the block 11. Electrode 12 is arranged to be in intimate electrical conduction with the pores of the body 11. Electrode 16 is in intimate conduction with the pores formed by the fine insulating media 14 and electrode 17 effectively forms a cylindrical shield around the interface between the body 11 pores and the finer media 14 pores both of which are intimate electrical conduction. A resinous or similar fill 15 insulates, seals and protects the cable 10 to the electrode connections.

In operation when the soil is wet, moisture is drawn by capillary tension into the pores of the block 11 then some is drawn into the finer pores of the media 14 then maintaining equilibrium. As the surrounding soil dries, its matric tension rises causing the capillary film of larger pores of block 11 to break and dehydrate. Subsequently smaller pores dehydrate as the tension continues to rise which cause the electrical conductivity to fall progressively as more of the pores empty. As the pores formed by media 14 are sufficiently small, the matric tension does not exceed its capillary break down tension within the device operating range, so it remains saturated.

FIG. 1b illustrates a second preferred embodiment where the electrode 16 is formed as a coil of a predetermined number of windings positioned in the base of all insulating cup or shield 18 which in turn is positioned in the base of the cavity containing the common electrode 17. Preferably, the outer surface of the cup 18 engages with the lower end of the coil 17 and the coil forming the electrode 16 engages with an inner surface of the cup 18. The cup or shield 18 need not be porous but must be electrically insulating. The media 14 may be conveniently filled into the cup 18 after the electrode 16 has been placed therein but before the cup 18 has been placed into the cavity containing the electrode 17. Thereafter the remaining regions of the cavity may be filled with media 14. The arrangement described above and shown in FIG. 1b enables electrical resistance between the electrodes 16 and 17 to be increased to obtain an improved control over their cell constant during manufacture. Furthermore, the current path through the media 14 is increased, the surface area in contact with the media is also increased, and dimensional location is stabilised during assembly.

A second embodiment as illustrated in FIGS. 2a and 2b would have the same general arrangement but introduce a void between electrode 12 and the common electrode 17. The purpose of this void is to enable more of the conductive field between these electrodes to be forced out into the surrounding soil if left as a void or if filled with particles to form differing pore sizes to fine tune the matric tension to electrical resistance relationship to suit available porous body materials. It should be recognised that the arrangement illustrated in FIG. 1b might also be utilised in the embodiment of FIGS. 2a and 2b.

To isolate the associated electronic circuits from earth potential, a system of magnetic isolation is shown in FIG. 3, where each pair of electrodes is connected to the secondary winding of its separate transformer as Tm & Tc so that the resistance of each set of electrodes is derived from the reflected impedance in its primary winding, this influences the voltages which appear as Vm & Vc when excited by the common oscillator O.

For a given set of conditions it has been found that the relationship between the electrical resistance of soils and their horticulturally desirable moisture content varies to some extent with the character of different soils, increasing as the mean pore size decreases, so the device SS is provided to enable the user to select by its description a moisture set point to suit the prevailing soil type.

The areas and geometry of the electrode sets 12–17 and 16–17 are selected to physically establish a stable intimate contact with the media and each may consist of more than one electrode, any of which may be interconnected.

In practice, the soil solution within the media 14 sets up an electrical resistance between the electrodes 16 & 17 which controls the impedance of secondary Tc and when excited by the alternating output from oscillator O, the reflected impedance of the primary winding, causes a decrease in the voltage Vc as the solution conductivity (EC) within nedia 14 increases, or in reverse. This function establishes the EC reference for the moisture set point MSP. This signal because of its relationship to the concentration of ions in solution can be used as a marker for nutrients and used for control of nutrient injection on demand during irrigation.

As the soil dries its matric tension rises causing progressive dehydration of the pores between electrodes 12 & 17 causing the electrical resistance between them to rise, increasing the impedance of the secondary Tm and the reflected impedance in its primary winding causing the voltage Vm to increase. Depending on the ratio set by Soil Select SS the voltage Vm increases until it reaches Moisture Set Point (MSP) which then enables Signal Processing Unit (SPU) to close the Irrigation Disable Contacts (IDC) permitting the irrigation control to proceed with its sequence when next programmed to do so.

The claims defining the invention are as follows:

1. A soil moisture sensing device including a body formed from porous material which, in use, is placed in intimate hydraulic conduction with soil in a surveillance area, said body forming a first zone having pore sizes that approximate a range of pores in typical soils, a second zone being formed within said first zone having pores arranged to be small enough to remain hydrated at matric tensions of the soil solution significantly above those which cause the first zone to dehydrate, said first zone containing a first electrode and said second zone containing a second electrode, each of which are paired with an electrode common to both said zones whereby, as the matric tension of the soil solution in the soil in the surveillance area increases, the pores within the first zone progressively dehydrate causing electrical resistance between the first electrode and the common electrode to progressively increase while the pores in the second zone remain hydrated such that the electrical resistance between the second electrode and the common electrode changes only in response to conductivity of the soil solution in the pores of the second zone.

2. A soil moisture sensing device in accordance with claim 1, wherein the common electrode is configured to provide a shield between the first and second electrodes.

3. A soil moisture sensing device in accordance with claim 1, wherein the first and second electrodes paired with the common electrode, are electrically isolated from associated electronic circuitry.

4. A soil moisture sensing device in accordance with any one of claims 1 to 3, wherein the electrodes, in either said zone or both said zones includes more than one electrode member.

5. A soil moisture sensing device in accordance with any one of claims 1 to 3, wherein the common electrode is formed as a helical coil or electrically conductive porous cylinder.

6. A soil moisture sensing device in accordance with any one of claims 1 to 3, wherein the common electrode is in the form of a cylindrical, electrically conductive mesh.

7. A soil moisture sensing device in accordance with any one of claims 1 to 3, wherein the resistance between the second electrode and the common electrode is used with a cell constant to indicate the concentration of ions in solution as a marker of its nutrient adequacy.

8. A soil moisture sensing device in accordance with any one of claims 1 to 3, wherein a void is introduced between the first electrode of the first zone and the common electrode to be used to modify electrical resistance to matric tension response of the sensing device.

9. A soil moisture sensing device in accordance with claim 8, wherein the void includes a porous material.

10. A soil moisture sensing device in accordance with any one of claims 1 to 3, wherein the second zone is formed by a cavity in the body formed from porous material, said second zone being filled with media providing a reduced pore size relative to said first zone.

11. A soil moisture sensing device in accordance with claim 10, wherein the second electrode and said common electrode are both located in the cavity forming said second zone with said common electrode generally surrounding said second electrode.

12. A soil moisture sensing device in accordance with claim 11, wherein said second electrode extends through said cavity forming the second zone with the common electrode being formed as a coil with a plurality of windings, or an electrically conductive porous cylinder, generally surrounding said second electrode.

13. A soil moisture sensing device in accordance with claim 11, wherein the second electrode is formed by a coil with one or more windings, and an electrically insulating member is provided between the windings of said second electrode and said common electrode.

14. A soil moisture sensing device in accordance with claim 13, wherein said electrically insulating member is a sleeve with the second electrode located inwardly of said sleeve and at least part of the common electrode located externally of said sleeve.

15. A soil moisture sensing device in accordance with claim 13, wherein said electrically insulating member is cup shaped with the second electrode located inwardly of said cup shaped member and at least part of the common electrode located externally of said cup shaped member.

* * * * *